United States Patent
Salloum

(10) Patent No.: US 11,246,730 B2
(45) Date of Patent: Feb. 15, 2022

(54) FLEXIBLE WEARABLE FOOT SLING

(71) Applicant: Miriam Y. Salloum, Asheville, NC (US)

(72) Inventor: Miriam Y. Salloum, Asheville, NC (US)

(*) Notice: Subject to any disclaimer, the term of this patent is extended or adjusted under 35 U.S.C. 154(b) by 116 days.

(21) Appl. No.: 16/287,932

(22) Filed: Feb. 27, 2019

(65) Prior Publication Data
US 2019/0192329 A1 Jun. 27, 2019

Related U.S. Application Data

(63) Continuation-in-part of application No. 14/881,812, filed on Oct. 13, 2015, now abandoned.

(51) Int. Cl.
*A61F 5/01* (2006.01)
*A61F 5/37* (2006.01)
*A61F 13/06* (2006.01)

(52) U.S. Cl.
CPC .............. *A61F 5/0127* (2013.01); *A61F 5/37* (2013.01); *A61F 13/064* (2013.01)

(58) Field of Classification Search
CPC ............ A61F 5/01–0104; A61F 5/0111; A61F 5/0127; A61F 5/37; A61F 13/06; A61F 13/064–069; A61F 13/063; A61F 5/0113; A61F 5/019; A61F 5/0195; A61F 13/08; A61F 13/085; A41B 11/00; A41B 11/003–005; A41B 11/007; A41B 11/08; D04B 9/46–56; A43B 7/26
See application file for complete search history.

(56) References Cited

U.S. PATENT DOCUMENTS

| | | | | | |
|---|---|---|---|---|---|
| 1,999,929 | A | * | 4/1935 | Hearn ..................... | A41B 11/08 2/239 |
| 3,128,763 | A | * | 4/1964 | Langenfeld .......... | A41B 11/004 128/894 |
| 5,099,860 | A | * | 3/1992 | Amrein ................. | A61F 5/0111 128/882 |
| 6,641,550 | B1 | * | 11/2003 | Johnson ................ | A61F 5/0111 602/65 |
| 7,828,759 | B2 | * | 11/2010 | Arensdorf ............... | A61F 5/019 2/239 |
| 9,421,118 | B2 | * | 8/2016 | Cropper .................. | A61F 5/042 |

(Continued)

*Primary Examiner* — Michelle J Lee
(74) *Attorney, Agent, or Firm* — William G. Heedy; The Van Winkle Law Firm

(57) ABSTRACT

A wearable foot sling for providing focal compression to portions of a wearer's foot, toes and leg, includes a sock member formed from an elastomeric fabric; a plantar surface portion having a thickened fabric pad; a plurality of tubes configured for engaged passage of the wearer's toes; a plurality of longitudinal fibers connecting the plurality of tubes with the thickened fabric pad; a circumferential band forming a tension path beginning at a dorsum portion, wrapping laterally around at a lateral longitudinal arch portion and gradually widening as it runs medially at a medial longitudinal arch portion, and continuing upwards toward the dorsum portion to form a closed loop; the circumferential band continuing laterally and superior across an anterior ankle joint portion, wrapping around a lower tibia portion and spiraling to the top of the sock member; and wherein the circumferential band applies tension along the tension path.

8 Claims, 10 Drawing Sheets

(56) References Cited

U.S. PATENT DOCUMENTS

| | | | |
|---|---|---|---|
| 2008/0255490 A1* | 10/2008 | Daley | A61F 5/0111 602/30 |
| 2009/0178178 A1* | 7/2009 | Nemcik | A61F 5/019 2/239 |
| 2012/0100778 A1* | 4/2012 | Cho | A41D 1/06 450/95 |
| 2012/0238929 A1* | 9/2012 | Grunden | A61F 5/0111 602/27 |
| 2017/0007465 A1* | 1/2017 | Edwards | A61F 13/068 |

* cited by examiner

FLEXIBLE WEARABLE FOOT SLING

RELATED APPLICATIONS

This patent application is a Continuation-In-Part Patent Application relating to and claiming the benefit of U.S. Non-Provisional patent application Ser. No. 14/881,812 filed on Oct. 13, 2015, which claims priority to and incorporates entirely by reference U.S. Provisional Patent Application Ser. No. 62/063,139 filed on Oct. 13, 2014.

FIELD OF THE INVENTION

This invention relates to medical devices and, more particularly, medical devices that support and assist individuals with musculoskeletal foot pain.

BACKGROUND OF THE INVENTION

Human feet and ankles bear the brunt of every step we take. Women in particular wear uncomfortable, jarring yet fashionable shoes that can do damage to the structure of the foot over time. Athletes are also at risk of heightened foot problems from traumatic injury, joint, tendon, or ligament problems.

Both arthritis and foot pain are major public health problems. Approximately 24% of adults have foot ailments, and the prevalence increases with age. Surprisingly, this topic of musculoskeletal foot pain has received little attention in the rheumatology community.

Some of the most common foot problems experienced by individuals include, but are not limited to, foot and ankle trauma/fractures, ligament sprains/tendonitis, Achilles tendon problems, heel pain/plantar fasciitis, bunions, hammertoes or claw toes, ankle or foot arthritis and flat feet deformities, among other problems.

Despite the major focus of structure and alignment in arthritis, remarkably little work has focused on the foot and nonsurgical foot interventions that might affect lower extremity joint alignment, structure and pain in rheumatic diseases. Emerging research suggests that there may be a significant role for foot orthotics and footwear in the treatment of rheumatoid arthritis, osteoarthritis of the hip, knee and foot and other commonly experienced conditions associated with musculoskeletal foot pain.

Because of these and other problems in the art, described herein, among other things, is a wearable foot sling for the relief of musculoskeletal foot pain comprised of materials possessing elastomeric properties that mimic the anatomical structures of the foot. In certain embodiments, the wearable foot sling described herein mimics the anatomical structures of the foot that may support the medial longitudinal arch and enhance the windlass mechanism during the late stance and push off phases of gait.

SUMMARY OF THE INVENTION

In accordance with one form of this invention, there is provided a wearable foot sling for providing focal compression to portions of a wearer's foot, toes and leg, the foot sling including a sock member being formed from a first elastomeric material and surrounding a cavity sized for receipt of the foot, toes and leg of the wearer; a plantar surface portion having a thickened fabric pad forming a metatarsal bar; a plurality of tubes each being sized and configured for engaged receipt and passage therethrough of the wearer's toes; an interdigit barrier separating each of the plurality of tubes; a plurality of longitudinal fibers connecting the plurality of tubes with the thickened fabric pad; a circumferential band that is integrally formed with the sock member; the circumferential band forming a tension path beginning at a dorsum portion, wrapping laterally around at a lateral longitudinal arch portion and gradually widening as it runs medially at a medial longitudinal arch portion, and continuing upwards toward the dorsum portion medially to connect with itself, thereby forming a closed loop; the circumferential band continuing laterally and superior across an anterior ankle joint portion, wrapping around a lower tibia portion; the circumferential band spiraling in a superior direction to the top of the sock member; and wherein the circumferential band applies tension along the tension path to the wearer's foot and leg.

In accordance with another form of this invention, there is provided a wearable foot sling for providing focal compression to portions of a wearer's foot, toes and leg, the foot sling including a sock member surrounding a cavity sized for receipt of the foot, toes and leg of the wearer; a plantar surface portion having a thickened fabric pad forming a metatarsal bar; a plurality of tubes each being sized and configured for engaged receipt and passage therethrough of the wearer's toes; an interdigit barrier separating each of the plurality of tubes; a plurality of longitudinal fibers connecting the plurality of tubes with the thickened fabric pad; a circumferential band that is integrally formed with the sock member; the circumferential band forming a tension path beginning at a dorsum portion, wrapping laterally around at a lateral longitudinal arch portion and gradually widening as it runs medially at a medial longitudinal arch portion, and continuing upwards toward the dorsum portion medially to connect with itself, thereby forming a closed loop; the circumferential band continuing laterally and superior across an anterior ankle joint portion, wrapping around a lower tibia portion; the circumferential band spiraling in a superior direction to the top of the sock member; and wherein the circumferential band applies tension along the tension path to the wearer's foot and leg.

In accordance with another form of this invention, there is provided a wearable foot sling for providing focal compression to portions of a wearer's foot, toes and leg, the foot sling including a sock member being formed from a first elastomeric material having a first tension force and surrounding a cavity sized for receipt of the foot, toes and leg of the wearer; a plantar surface portion having a thickened fabric pad forming a metatarsal bar; a plurality of tubes each being sized and configured for engaged receipt and passage therethrough of the wearer's toes; an interdigit barrier separating each of the plurality of tubes; a plurality of longitudinal fibers connecting the plurality of tubes with the thickened fabric pad; the longitudinal fibers extending longitudinally between the plurality of tubes at a proximal phalanx portion and the heel portion; a circumferential band being formed from a second elastomeric material having a second tension force that is woven into the first elastomeric material of the sock member; wherein the second tension force is greater than the first tension force; the circumferential band forming a tension path beginning at a dorsum portion, wrapping laterally around at a lateral longitudinal arch portion and gradually widening as it runs medially at a medial longitudinal arch portion, and continuing upwards toward the dorsum portion medially to connect with itself, thereby forming a closed loop; the circumferential band continuing laterally and superior across an anterior ankle joint portion, wrapping around a lower tibia portion; the circumferential band spiraling in a superior direction to the top of the sock member; and wherein the circumferential band applies tension along the tension path to the wearer's foot and leg.

BRIEF DESCRIPTION OF THE DRAWINGS

The invention may be better understood in reference to the following description taken in conjunction with the accompanying drawings in which.

Like reference numerals refer to like parts throughout the several views of the drawings.

DETAILED DESCRIPTION OF THE PREFERRED EMBODIMENTS

In general, the wearable foot sling (101) disclosed herein is designed to address relief of musculoskeletal foot pain and is designed for comfort and compatibility with most shoes worn, including low profile dress and sport shoes.

Figure 1:
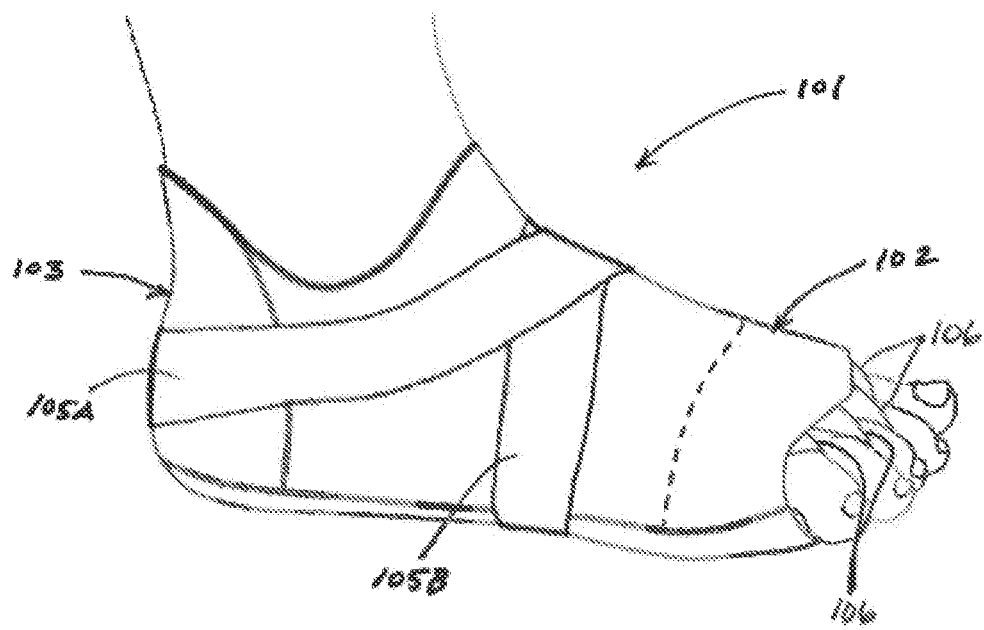
FIG. 1 shows a perspective view of an embodiment of the flexible wearable foot sling.
Figure 2:
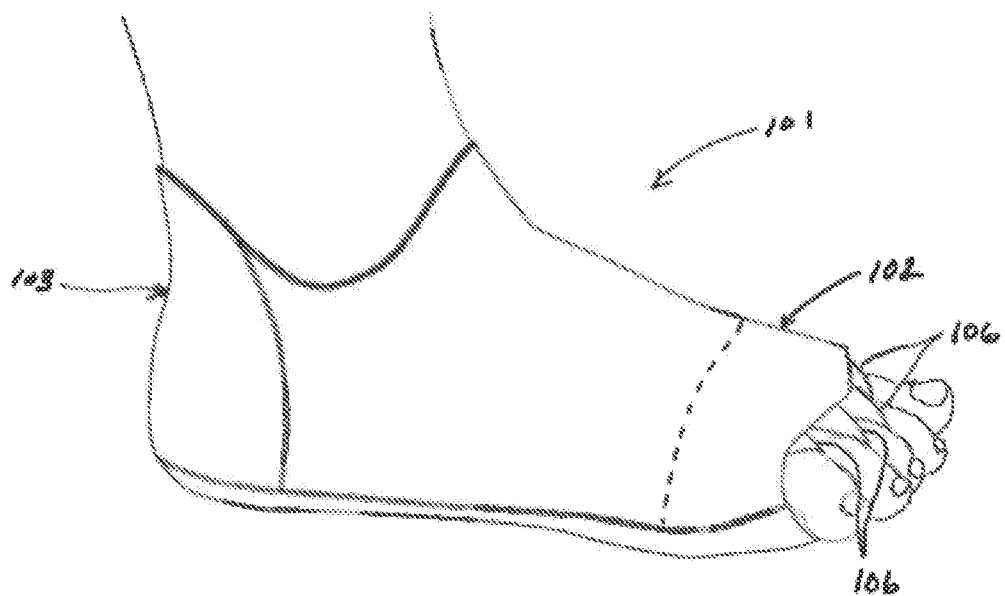
FIG. 2 shows a perspective view of an embodiment of the flexible wearable foot sling.
Figure 3:
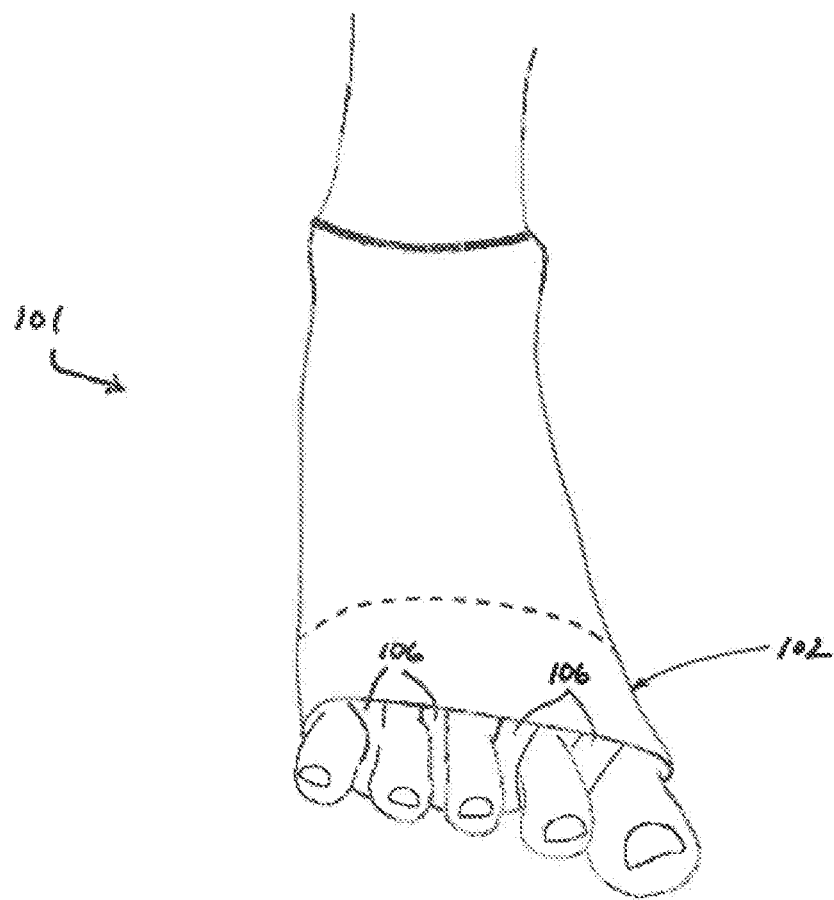
FIG. 3 shows a perspective view of an embodiment of the flexible wearable foot sling.

In certain embodiments, the wearable foot sling (101) will be comprised of a conforming material with elastomeric properties known to those of ordinary skill in the art. Contemplated materials include, but are not necessarily limited to, neoprene, polychloroprenes and other known synthetic rubbers with elastomeric properties. In one embodiment, as depicted in FIGS. 1-2, the wearable foot sling (101) is comprised of a tight-fitting sling (101), the sling (101) having a front end (102) which is comprised of webbing (106) that fits over the interdigit spaces of toes 1-5 and a back end (103) which is secured over the posterior heel. Once the sling (101) is positioned in place on a user's foot, the sling (101) functions to restrain the longitudinal lengthening of soft tissues between a user's toes and heel, effectively shortening the fibers of the plantar fascia.

In certain alternative embodiments, the sling (101) will include bands of elastomeric properties aligned in parallel with the metatarsals that will augment the shortening effect applied by the sling (101). In general, any material known to those of ordinary skill in the art with elastomeric properties is contemplated as a possible band aligned in parallel with the metatarsals.

Figure 4:
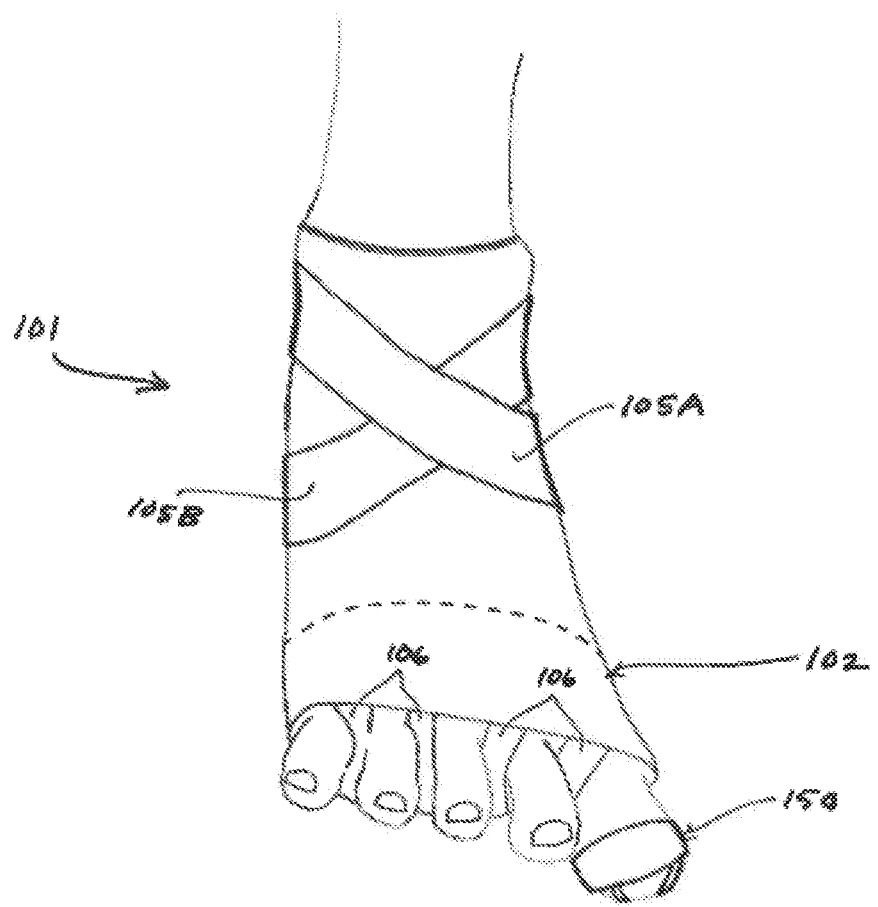
FIG. 4 shows a perspective view of an embodiment of the flexible wearable foot sling.
Figure 5:
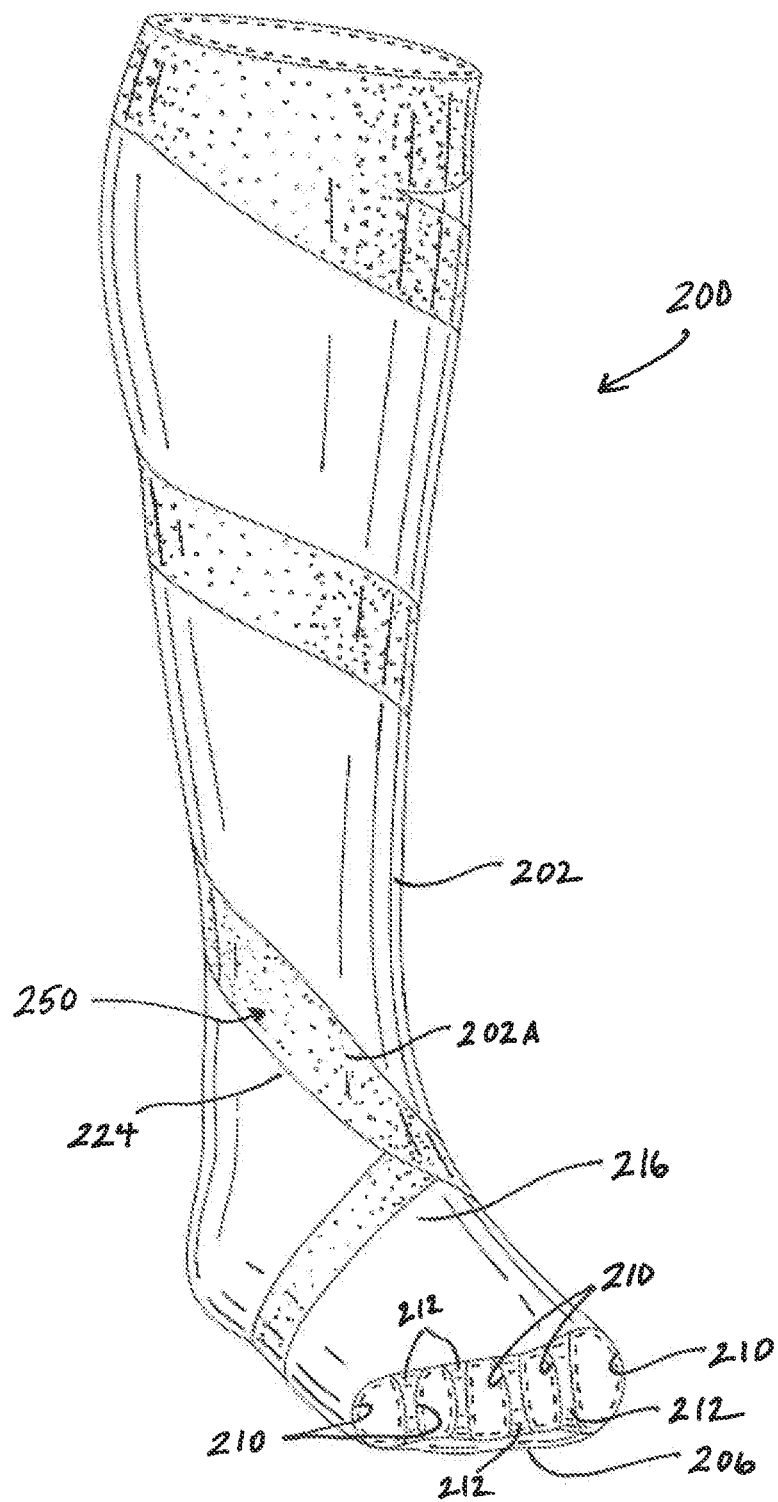
FIG. 5 shows a perspective view of an embodiment of the flexible wearable foot sling.
Figure 6:
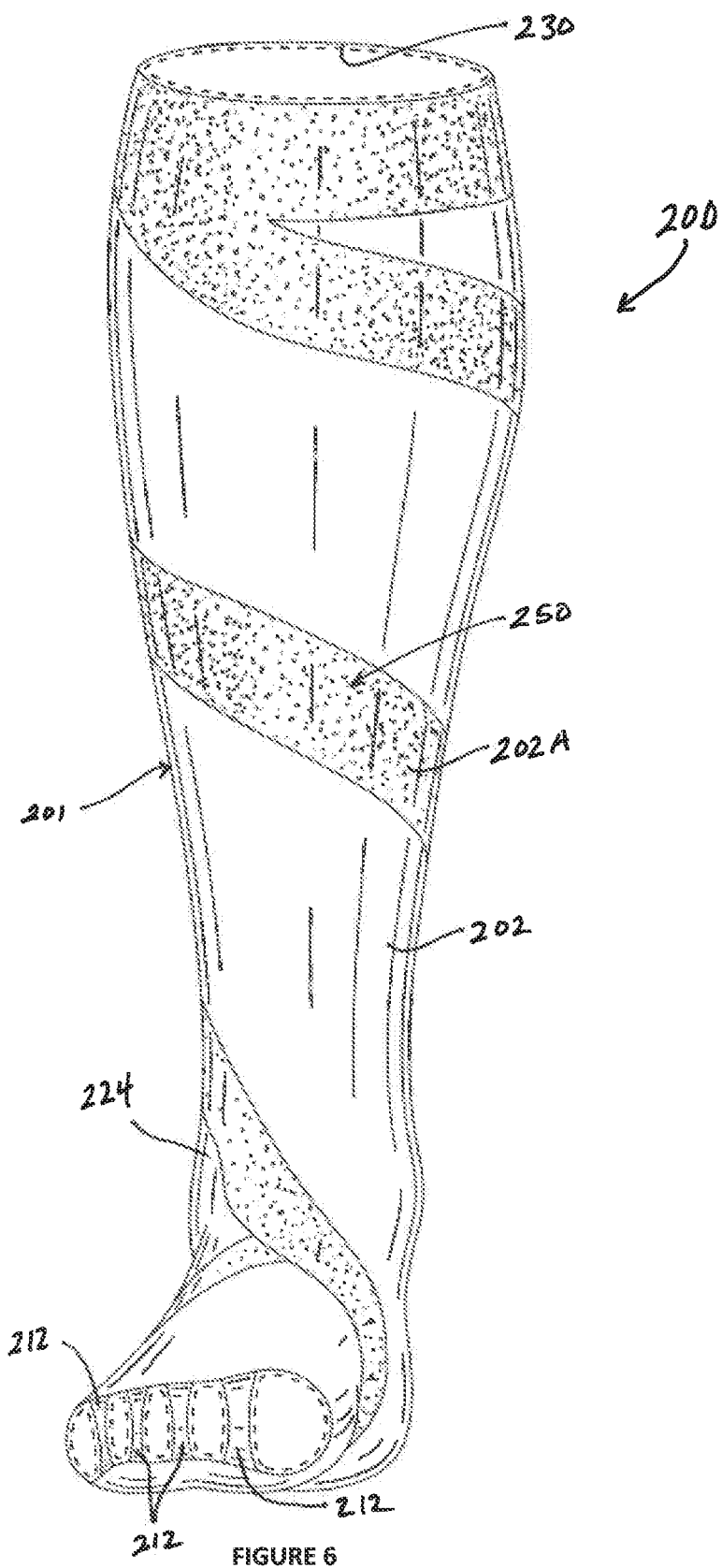
FIG. 6 shows a front elevational view of the flexible wearable foot sling in accordance with the embodiment illustrated in FIG. 5.
Figure 7:
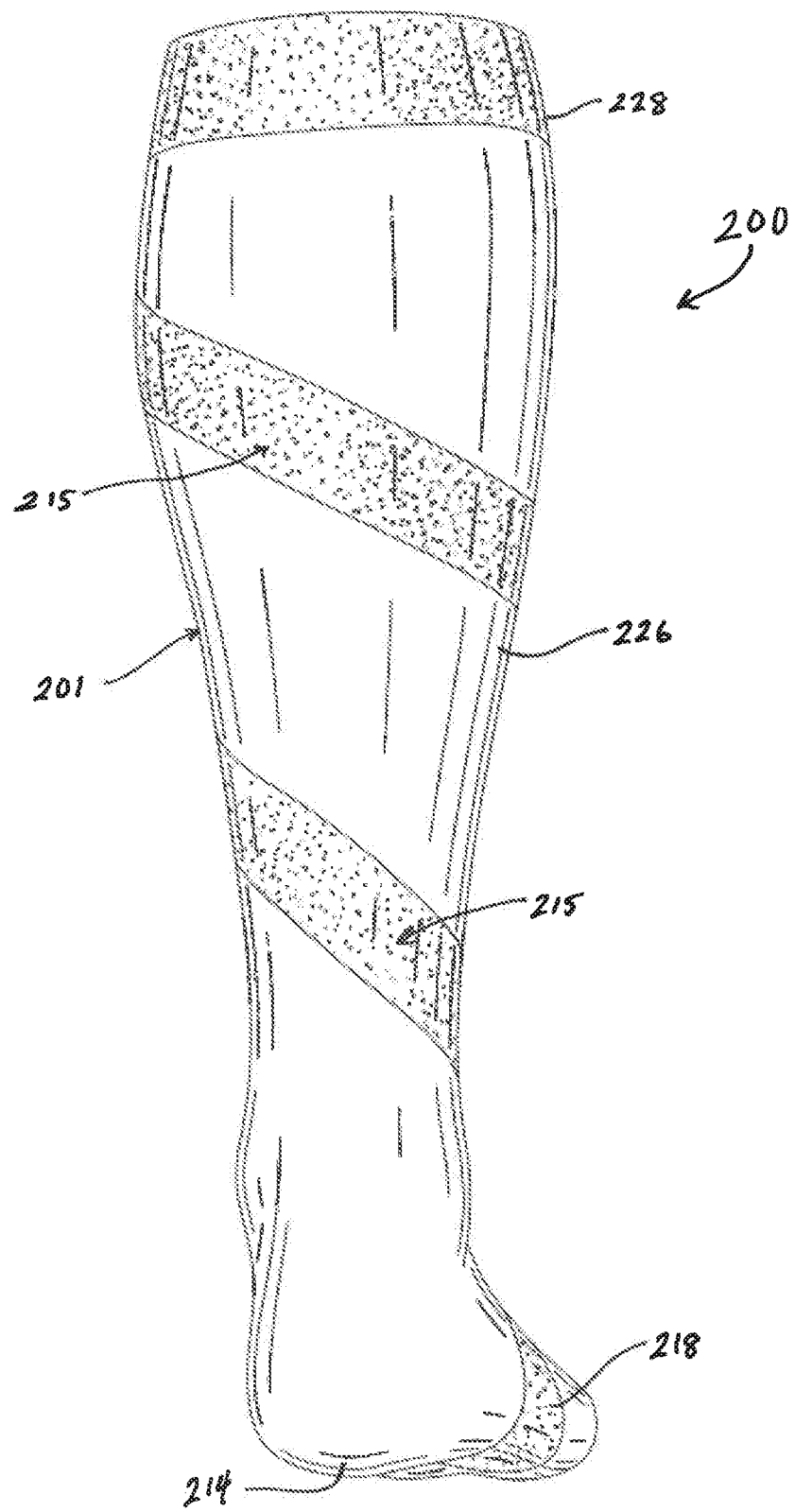
FIG. 7 shows a rear elevational view of the flexible wearable foot sling in accordance with the embodiment illustrated in FIG. 5.
Figure 8:
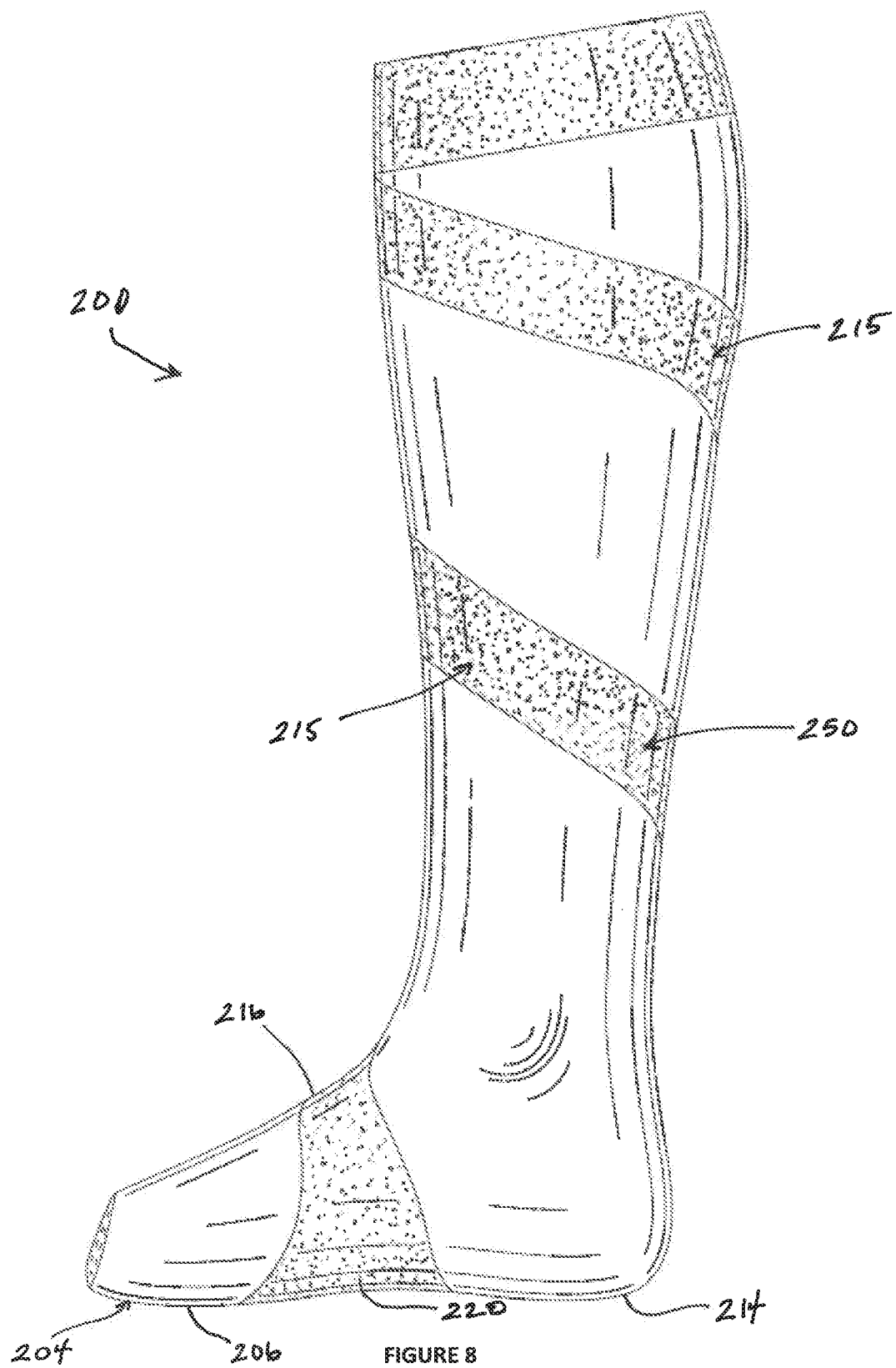
FIG. 8 shows a right side elevational view of the flexible wearable foot sling in accordance with the embodiment illustrated in FIG. 5.
Figure 9:
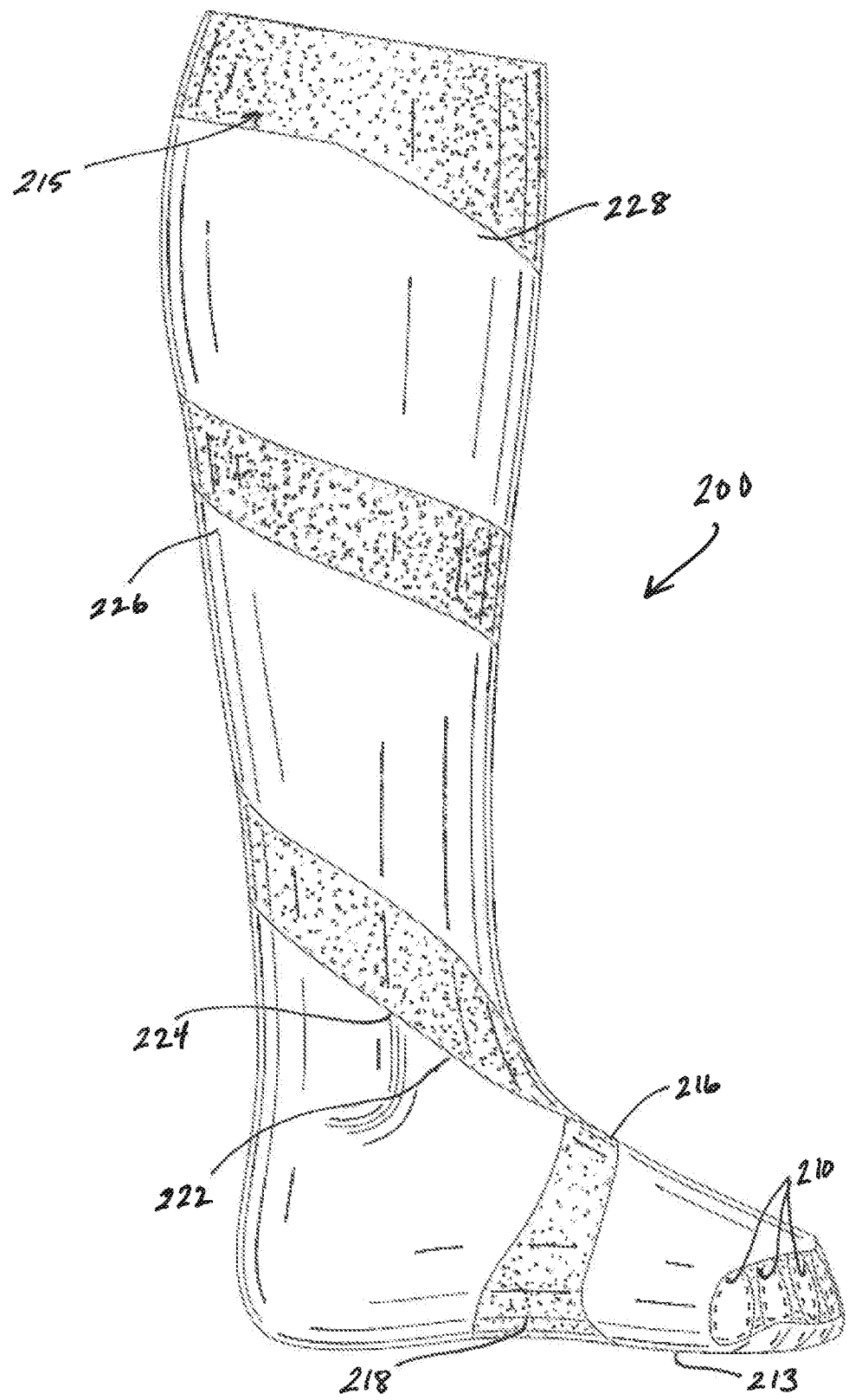
FIG. 9 shows a left side elevational view of the flexible wearable foot sling in accordance with the embodiment illustrated in FIG. 5.
Figure 10:
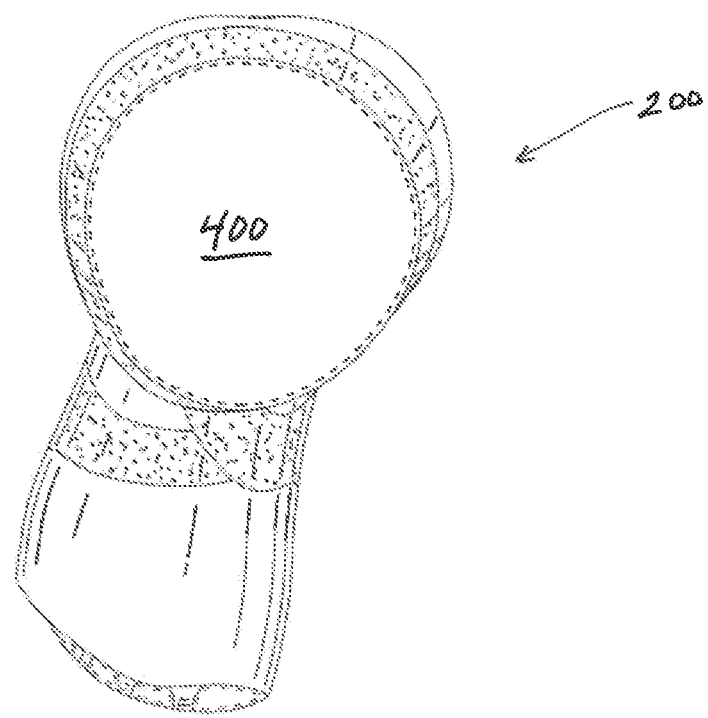
FIG. 10 shows a top plan view of the flexible wearable foot sling in accordance with the embodiment illustrated in FIG. 5.
Figure 11:
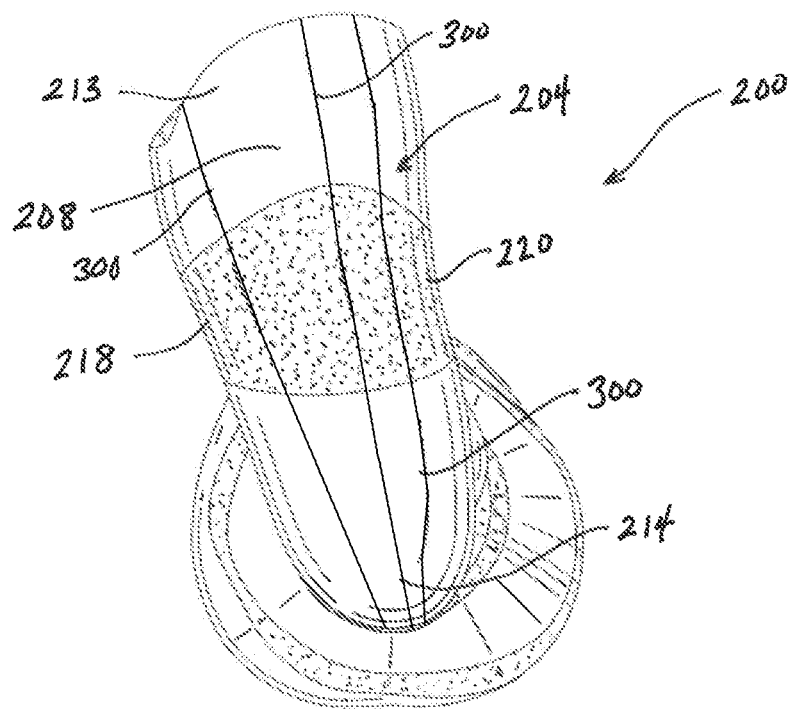
FIG. 11 shows a bottom plan view of the flexible wearable foot sling in accordance with the embodiment illustrated in FIG. 5.
Figure 12:
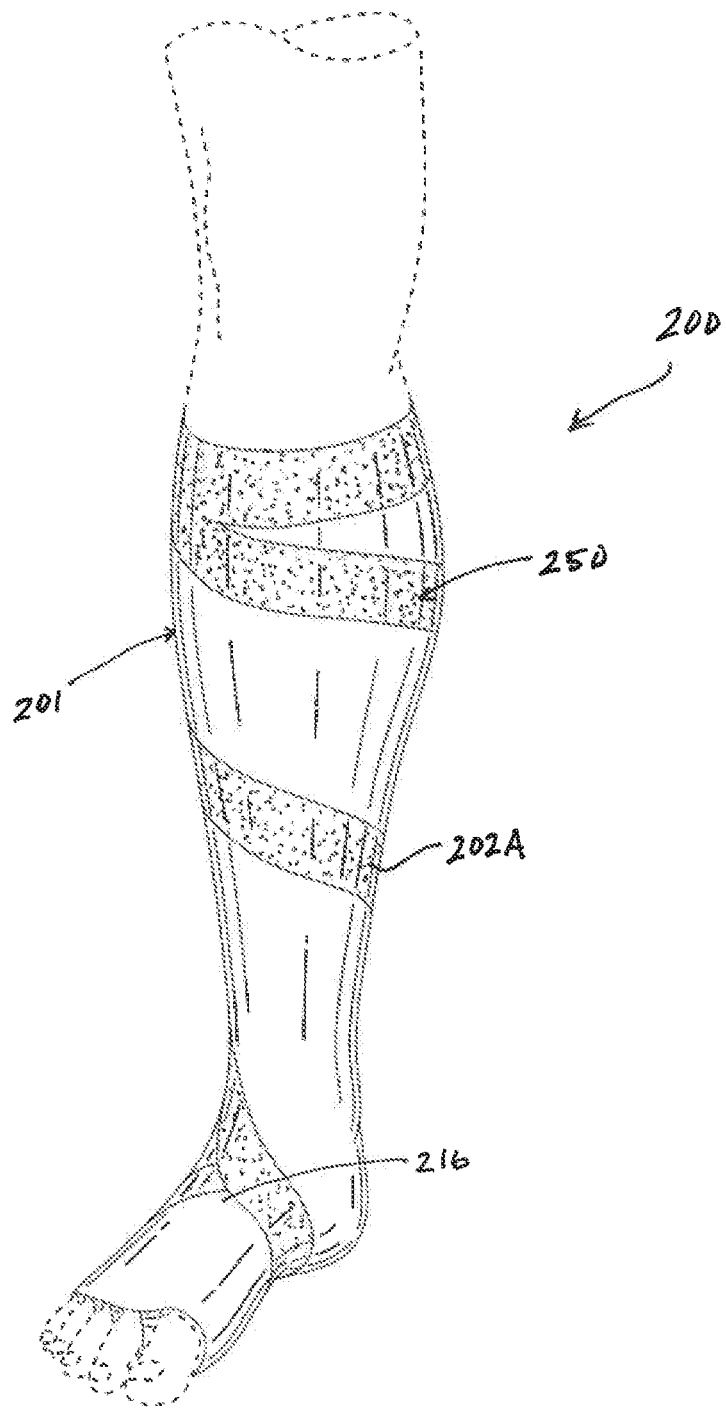
FIG. 12 shows a perspective view of the flexible wearable foot sling in accordance with the embodiment illustrated in FIG. 5 being worn by a user.

In other embodiments of the sling (101), there will be a pair of diagonally oriented supports (105A, 105B) that cross under the plantar midfoot to further support the medial longitudinal arch. In certain embodiments, as demonstrated in FIGS. 1 and 4, the diagonally oriented supports (105A, 105B) will also cross diagonally on the top of the foot and sling (101), although this orientation is not determinative. As depicted in FIGS. 1 and 4, the medial longitudinal diagonally oriented supports (105A, 105B) will likely be secured over the dorsum of the foot by fastening means known to those of ordinary skill in the art including, but not limited to, hook and loop fastener, clips, hooks, ties, fasteners, knots, and loops. In one embodiment, the diagonally oriented supports (105A, 105B) are made from an elastomeric material.

In certain additional embodiments, an additional element of the sling (101) is a smaller sling system around the first phalanx of the great toe, the phalanx sling (150). As demonstrated in FIG. 4, the phalanx sling (150) is comprised of a single support that attaches to the bottom of the sling (101) at the base of the great toe, wraps around the front of the great toe and then crosses back over itself to attach to the bottom of the sling (101) at the base of the great toe on the opposite side. Accordingly, the phalanx sling (150) wraps around the front of the toe and forms a cross and attaches to the bottom of the sling near the great toe. In general, the function of the phalanx sling (150) is to improve plantar flexion during loading. It should be understood that this phalanx sling (150) may be optional, and could be reversed (i.e., the phalanx sling may be wrapped around the great toe in the opposite manner than demonstrated in FIG. 4) to enhance dorsiflexion.

In sum, the orientation of the sling (101) provided herein creates a multi-point harness which shortens and restricts the motion of the plantar structures of the foot in a triplanar manner, thereby decreasing abnormal tension in muscle, fascia, and neural pathways. As such, this device is similar in purpose to both the molded and non-molded foot orthoses of the prior art which are utilized for decreasing foot pain.

However, the sling (101) described herein has numerous advantages over these designs of the prior art. First, as demonstrated in FIGS. 1-4, the sling (101) has a lower profile, fitting snugly with the foot. This lowered profile allows compatibility between the sling (101) and most shoe designs. Further, unlike the designs of the prior art, because of its low profile a user can use the sling generally without removing the original insoles of the shoes. Second, the sling offers the possibility for increased customer compliance and more frequent use than the currently utilized methodologies due to decreased sense of difficulty with use (compared to prior art technologies) and increased sense of comfort. Third, due to its simple design, the sling (101) is more reasonably priced than the custom foot orthoses of the prior art. In addition, the currently utilized over-the-counter and custom orthoses frequently have to be accommodated by either the purchase of a separate pair of shoes to account for increased depth and width of the orthoses materials, also adding to the cost. As noted previously, this is not necessary with the disclosed sling (101). Finally, another issue with current foot orthoses utilized in the art is the incompatibility of a person's foot function and the density and contours of the materials comprising the orthoses. Pain, discomfort and blisters are frequent results of such issues with errors in fit and material density. Non-compliance by patients due to discomfort and cost caused by the orthoses of the prior art is a frequently cited drawback in some studies on foot pain and orthoses.

In certain embodiments, the sling (101) disclosed herein will be utilized as follows. In a first step, the front end (102) of the sling, which is comprised of webbing (106) that fits over the interdigit spaces of toes 1-5, is placed in the interdigit spaces of a user's toes. Generally this first step is performed while the user is in a non-weight bearing position (e.g., sitting). In a second step, the back end (103) of the sling (101) is secured over the user's posterior heel, bringing the sling into a snug, taut and comfortable position on the bottom of a user's foot. In a third step, the user secures the diagonally oriented supports (105A, 105B) (proximal/lateral to distal/medial and distal/lateral to proximal/medial midfoot) to create a hammock for the navicular. In a fourth step, in the embodiments of the sling (101) with a phalanx sling (150), the phalanx sling (150) is positioned into place around the great toe. In these embodiments, this phalanx sling assists the proximal phalanx of the first toe in plantar flexion, but does not necessarily restrict overall mobility. As noted previously, this phalanx sling (150) may be reversed to the dorsum or removed based on the comfort to the customer.

Referring now to FIGS. 5-12, another embodiment of the wearable foot sling (200) is shown and includes a sock member (201) that is primarily formed from a first elastomeric fabric (202) surrounding a cavity (400) that is sized and configured for receipt of a wearer's foot, toes, and a portion of the wearer's leg.

At the plantar surface portion (204) of the sling (200) there is a thicker weave forming a thickened fabric pad (206) having a thickness greater than the elastomeric fabric (202). The thickened fabric pad (206) is positioned proximal the metatarsal heads of the wearer's foot and is sized and configured for serving as a metatarsal bar (208) to create an unloading effect on the metatarsal heads. The thickened fabric pad (206) connects with a plurality of longitudinal fibers (300) of the plurality of tubes (210), separating the wearer's toes, thereby addressing issues of sesamoiditis, metatarsalgia, and plantar fasciitis.

The tubes (210) are formed of thickened fabric and are sized and configured for engaged receipt and passage therethrough of the wearer's toes, which are separated individually by interdigit barriers (212), thereby leaving the digits of the wearer's foot either exposed. In some embodiments of the sling (200) a light weave may be included to cover the wearer's toes (not shown). The main function of the interdigit barriers (212) between the toes (between the base of the proximal phalanx) is to increase the space between the metatarsal heads in a longitudinal manner and to decrease impingement of the interdigital nerves (such as with Morton's neuroma and metatarsalgia). In one embodiment, the longitudinal fibers (300) extend longitudinally between the plurality of tubes (210) at a proximal phalanx portion (213) and the heel portion (214) will further unload the plantar fascia and intrinsic foot muscles by shortening in the sagittal. This will be an additional plane by which the plantar soft tissue is unloaded, which will assist the circumferential band (250) that primarily serves to unload in the frontal plane.

The circumferential band (250) is integrally formed with the sock member (201) as part of the sling (200) formed from a second elastomeric material (202A) provides increased tension along a tension path (215) on the wearer relative to the tension supplied by the elastomeric fabric (202). In one embodiment, the circumferential band (250) is woven into the elastomeric fabric (202) of the sling (200). The circumferential band (250) starts on the dorsum portion (216) of the sling (200), wraps laterally around at the lateral longitudinal arch portion (218) and gradually widens as it runs medially at the medial longitudinal arch portion (220), and continues back up toward the dorsum portion (216) medially to partially connect to the starting point, thereby creating a closed loop. From there, the band (250) partially continues laterally and superior to cross the anterior ankle joint portion (222), wrapping around the distal lateral aspect of the lower tibia portion (224), located just above the lateral malleolus of the wearer, and continues to wrap around diagonally from the lateral to medial aspect of the lower tibia portion (224) as it spirals in a superior direction to the top (230) of the sling (201). This upward spiraling weave will effectively cinch the soft tissue structure of the wearer at the posterior medial compartment portion (226), adjacent the soleus, flexor digitorum longus and posterior tibialis muscles of the wearer, to the tibial periosteum portion (228). This diagonal compression of these muscles toward the tibia will address bony traction injuries like medial tibial stress syndrome and foot/ankles pain of posterior tibialis tendinopathy. Focal and specific compression of these muscles mimic successful athletic taping techniques demonstrated in the research.

Generally, the sling (200) uses a focal fabric weave with high levels of compression in diagonal patterns, therefore mimicking the triplanar motion of the foot and lower leg versus just straight planes of compression typically seen with other designs. This design makes the strapping system more biomechanically effective for treating foot/ankle/lower leg pain. Moreover, the strapping system of this higher compression weave is made more focal and concentrated with unloading the specific structures of the foot/lower leg mentioned above due to it being surrounded by a less compressive weave. This makes a true "strap" system with defined areas of compression and control.

While the invention has been disclosed in connection with certain preferred embodiments, the elements, connections, and dimensions of the preferred embodiments should not be understood as limitations on all embodiments. Modifications and variations of the described embodiments may be made without departing from the spirit and scope of the invention, and other embodiments should be understood to be encompassed in the present disclosure as would be understood by those of ordinary skill in the art.

What is claimed is:

1. A wearable foot sling for providing focal compression to portions of a wearer's foot, toes and leg, the foot sling comprising:
a sock member surrounding a cavity sized for receipt of the foot, toes and leg of the wearer, the sock member further comprising a forefoot opening; a plantar surface portion of the sock member having a thickened fabric pad forming a metatarsal bar; a plurality of tubes each being sized and configured for engaged receipt and passage therethrough of the wearer's toes, the plurality of tubes being within the sock member and having openings aligned with the forefoot opening of the sock member, such that when the foot sling is worn, the toes of the wearer are exposed; an interdigit barrier separating each of the plurality of tubes; a plurality of longitudinal fibers connecting the plurality of tubes with the thickened fabric pad, wherein the plurality of longitudinal fibers are configured to extend longitudinally from the plurality of tubes at a proximal phalanx portion to a heel portion;

a circumferential band that is integrally formed with the sock member; the circumferential band forming a tension path configured to begin at a dorsum portion, configured to wrap laterally around at a lateral longitudinal arch portion and configured to gradually widen as it runs medially at a medial longitudinal arch portion, and configured to continue upwards toward the dorsum portion medially to connect with itself, thereby forming a closed loop; the circumferential band configured to continue laterally and superior across an anterior ankle joint portion, configured to wrap around a lower tibia portion; the circumferential band spiraling in a superior direction to a top portion of the sock member; and wherein the circumferential band is configured to apply tension along the tension path to the wearer's foot and leg.

2. The wearable foot sling of claim 1 wherein the sock member is formed from a first elastomeric material.

3. The wearable foot sling of claim 2, wherein the circumferential band is woven into the first elastomeric material of the sock member.

4. The wearable foot sling as recited in claim 2 wherein the first elastomeric material of the sock member has a first tension force; the circumferential band is formed from a second elastomeric material having a second tension force; and wherein the second tension force is greater than the first tension force.

5. A wearable foot sling for providing focal compression to portions of a wearer's foot, toes and leg, the foot sling comprising:

a sock member being formed from a first elastomeric material and surrounding a cavity sized for receipt of the foot, toes and leg of the wearer, the sock member further comprising a forefoot opening; a plantar surface portion of the sock member having a thickened fabric pad forming a metatarsal bar, wherein the thickened fabric pad has a thickness greater than the first elastomeric material; a plurality of tubes each being sized and configured for engaged receipt and passage therethrough of the wearer's toes, the plurality of tubes being within the sock member and having openings aligned with the forefoot opening of the sock member, such that when the foot sling is worn, the toes of the wearer are exposed; an interdigit barrier separating each of the plurality of tubes; a plurality of longitudinal fibers connecting the plurality of tubes with the thickened fabric pad, wherein the plurality of longitudinal fibers are configured to extend longitudinally from the plurality of tubes at a proximal phalanx portion to a heel portion;

a circumferential band that is integrally formed with the sock member; the circumferential band forming a tension path that is configured to begin at a dorsum portion, configured to wrap laterally around at a lateral longitudinal arch portion and configured to gradually widen as it runs medially at a medial longitudinal arch portion, and configured to continue upwards toward the dorsum portion medially to connect with itself, thereby forming a closed loop; the circumferential band configured to continue laterally and superior across an anterior ankle joint portion, configured to wrap around a lower tibia portion; the circumferential band spiraling in a superior direction to a top portion of the sock member; and wherein the circumferential band is configured to apply tension along the tension path to the wearer's foot and leg.

6. The wearable foot sling of claim 5 wherein the circumferential band is woven into the first elastomeric material of the sock member.

7. The wearable foot sling as recited in claim 5 wherein the first elastomeric material of the sock member has a first tension force; the circumferential band is formed from a second elastomeric material having a second tension force; and wherein the second tension force is greater than the first tension force.

8. A wearable foot sling for providing focal compression to portions of a wearer's foot, toes and leg, the foot sling comprising:

a sock member being formed from a first elastomeric material having a first tension force and surrounding a cavity sized for receipt of the foot, toes and leg of the wearer, the sock member further comprising a forefoot opening; a plantar surface portion of the sock member having a thickened fabric pad forming a metatarsal bar, wherein the thickened fabric pad has a thickness greater than the first elastomeric material; a plurality of tubes each being sized and configured for engaged receipt and passage therethrough of the wearer's toes, the plurality of tubes being within the sock member and having openings aligned with the forefoot opening of the sock member, such that when the foot sling is worn, the toes of the wearer are exposed; an interdigit barrier separating each of the plurality of tubes; a plurality of longitudinal fibers connecting the plurality of tubes with the thickened fabric pad; the plurality of longitudinal fibers configured to extend longitudinally from the plurality of tubes at a proximal phalanx portion to a heel portion;

a circumferential band being formed from a second elastomeric material having a second tension force that is woven into the first elastomeric material of the sock member;

wherein the second tension force is greater than the first tension force; the circumferential band forming a tension path configured to begin at a dorsum portion, configured to wrap laterally around at a lateral longitudinal arch portion and configured to gradually widen as it runs medially at a medial longitudinal arch portion, and configured to continue upwards toward the dorsum portion medially to connect with itself, thereby forming a closed loop; the circumferential band configured to continue laterally and superior across an anterior ankle joint portion, configured to wrap around a lower tibia portion; the circumferential band spiraling in a superior direction to a top portion of the sock member; and wherein the circumferential band is configured to apply tension along the tension path to the wearer's foot and leg.

* * * * *